United States Patent
Bernier

(10) Patent No.: US 9,066,479 B2
(45) Date of Patent: Jun. 30, 2015

(54) WATERMELON VARIETY WML-EJ11-2553

(71) Applicant: Seminis Vegetable Seeds, Inc., St. Louis, MO (US)

(72) Inventor: Jerome Bernier, St. Louis, MO (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 77 days.

(21) Appl. No.: 13/942,578

(22) Filed: Jul. 15, 2013

(65) Prior Publication Data

US 2015/0020228 A1    Jan. 15, 2015

(51) Int. Cl.
| | |
|---|---|
| *A01H 5/00* | (2006.01) |
| *A01H 5/10* | (2006.01) |
| *A01H 4/00* | (2006.01) |
| *A01H 1/00* | (2006.01) |
| *C12N 15/82* | (2006.01) |
| *C12N 5/04* | (2006.01) |
| *A01H 5/08* | (2006.01) |
| *A01G 1/00* | (2006.01) |
| *A01H 1/02* | (2006.01) |
| *A01H 1/04* | (2006.01) |

(52) U.S. Cl.
CPC ............ *A01H 5/08* (2013.01); *A01G 1/001* (2013.01); *C12N 15/8201* (2013.01); *A01H 1/02* (2013.01); *A01H 4/00* (2013.01); *A01H 1/04* (2013.01)

(58) Field of Classification Search
None
See application file for complete search history.

(56) References Cited

U.S. PATENT DOCUMENTS 8,212,118 B1 *   7/2012   Brusca et al. ................. 800/308

OTHER PUBLICATIONS

Fehr (Iowa State University, "Principles of Cultivar Development," vol. 1 Theory and Technique and vol. 2 Crop Species, Soybean, Macmillian Publishing Company, New York, pp. 360-376, 1987).*
Haun et al (Plant Physiology, Feb. 2011, vol. 155, pp. 645-655).*
Websters.com: definition of "occasional" (2014) http://dictionary.reference.com/browse/occasional?s=t, (Accessed on Nov. 6, 2014).*
Moose SP, Mumm RH., "Molecular plant breeding as the foundation for 21st century crop improvement", Plant Physiol.; 147(3):969-77; Jul. 2008.
Variety specific information as indicated in transmittal letter of Mar. 24, 2014 Information Disclosure Statement for U.S. Appl. No. 13/942,578.

* cited by examiner

*Primary Examiner* — David T Fox
*Assistant Examiner* — Lee A Visone
(74) *Attorney, Agent, or Firm* — Dentons US LLP; Alissa Eagle Esq.

(57) ABSTRACT

The invention provides seed and plants of the watermelon line designated WML-EJ11-2553. The invention thus relates to the plants, seeds and tissue cultures of watermelon line WML-EJ11-2553, and to methods for producing a watermelon plant produced by crossing a plant of watermelon line WML-EJ11-2553 with itself or with another watermelon plant, such as a plant of another line. The invention further relates to seeds and plants produced by such crossing. The invention further relates to parts of a plant of watermelon line WML-EJ11-2553, including the fruits and gametes of such plants.

22 Claims, No Drawings

WATERMELON VARIETY WML-EJ11-2553

FIELD OF THE INVENTION

The present invention relates to the field of plant breeding and, more specifically, to the development of watermelon line WML-EJ11-2553.

BACKGROUND OF THE INVENTION

The goal of vegetable breeding is to combine various desirable traits in a single variety/hybrid. Such desirable traits may include any trait deemed beneficial by a grower and/or consumer, including greater yield, resistance to insects or disease, tolerance to environmental stress, and nutritional value.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different genotypes produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

SUMMARY OF THE INVENTION

In one aspect, the present invention provides a watermelon plant of the watermelon line designated WML-EJ11-2553. Also provided are watermelon plants having all the physiological and morphological characteristics of watermelon line WML-EJ11-2553. Parts of the watermelon plant of the present invention are also provided, for example, including pollen, an ovule, scion, a rootstock, a fruit, and a cell of the plant.

The invention also concerns seed of watermelon line WML-EJ11-2553. The watermelon seed of the invention may be provided, in certain illustrative embodiments, as an essentially homogeneous population of watermelon seed of the line designated WML-EJ11-2553. Essentially homogeneous populations of seed are generally free from substantial numbers of other seed. Therefore, in one embodiment, seed of line WML-EJ11-2553 may be defined as forming at least about 97% of the total seed, including at least about 98%, 99%, or more of the seed. The population of watermelon seed may be particularly defined as being essentially free from hybrid seed. The seed population may be separately grown to provide an essentially homogeneous population of watermelon plants designated WML-EJ11-2553.

In another aspect of the invention, a plant of watermelon line WML-EJ11-2553 comprising an added heritable trait is provided. The heritable trait may comprise a genetic locus that is, for example, a dominant or recessive allele. In one embodiment of the invention, a plant of watermelon line WML-EJ11-2553 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a plant of line WML-EJ11-2553 is provided. The tissue culture will preferably be capable of regenerating plants capable of expressing all of the physiological and morphological characteristics of the line, and of regenerating plants having substantially the same genotype as other plants of the line. Examples of some of the physiological and morphological characteristics of the line WML-EJ11-2553 include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides watermelon plants regenerated from a tissue culture of the invention, the plants having all the physiological and morphological characteristics of line WML-EJ11-2553.

In yet another aspect of the invention, processes are provided for producing watermelon seeds, plants and fruits, which processes generally comprise crossing a first parent watermelon plant with a second parent watermelon plant, wherein at least one of the first or second parent watermelon plants is a plant of the line designated WML-EJ11-2553. These processes may be further exemplified as processes for preparing hybrid watermelon seed or plants, wherein a first watermelon plant is crossed with a second watermelon plant of a different, distinct line to provide a hybrid that has, as one of its parents, the watermelon plant line WML-EJ11-2553. In these processes, crossing will result in the production of seed. The seed production occurs regardless of whether the seed is collected or not.

In one embodiment of the invention, the first step in "crossing" comprises planting seeds of a first and second parent watermelon plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent watermelon plants into plants that bear flowers. A third step may comprise preventing self-pollination of the plants, such as by emasculating the flowers, (i.e., killing or removing pollen).

A fourth step for a hybrid cross may comprise cross-pollination between the first and second parent watermelon plants. Yet another step comprises harvesting the seeds from at least one of the parent watermelon plants. The harvested seed can be grown to produce a watermelon plant or hybrid watermelon plant.

The present invention also provides the watermelon seeds and plants produced by a process that comprises crossing a first parent watermelon plant with a second parent watermelon plant, wherein at least one of the first or second parent watermelon plants is a plant of the line designated WML-EJ11-2553. In one embodiment of the invention, watermelon seed and plants produced by the process are first generation (F1) hybrid watermelon seed and plants produced by crossing a plant in accordance with the invention with another, distinct plant. The present invention further contemplates plant parts of such an F1 hybrid watermelon plant, and methods of use thereof. Therefore, certain exemplary embodiments of the invention provide an F1 hybrid watermelon plant and seed thereof.

In still yet another aspect of the invention, the genetic complement of the watermelon plant line designated WML-EJ11-2553 is provided. The phrase "genetic complement" is used to refer to the aggregate of nucleotide sequences, the expression of which sequences defines the phenotype of, in the present case, a watermelon plant, or a cell or tissue of that plant. A genetic complement thus represents the genetic makeup of a cell, tissue or plant, and a hybrid genetic complement represents the genetic make up of a hybrid cell, tissue or plant. The invention thus provides watermelon plant cells that have a genetic complement in accordance with the watermelon plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that line WML-EJ11-2553 could be identified by any of the many well known techniques such as, for example, Simple Sequence Length Polymorphisms (SSLPs) (Williams et al., Nucleic Acids Res., 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., Science, 280:1077-1082, 1998).

In still yet another aspect, the present invention provides hybrid genetic complements, as represented by watermelon plant cells, tissues, plants, and seeds, formed by the combination of a haploid genetic complement of a watermelon plant of the invention with a haploid genetic complement of a second watermelon plant, preferably, another, distinct watermelon plant. In another aspect, the present invention provides a watermelon plant regenerated from a tissue culture that comprises a hybrid genetic complement of this invention.

In still yet another aspect, the invention provides a method of determining the genotype of a plant of watermelon line WML-EJ11-2553 comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In still yet another aspect, the present invention provides a method of producing a plant derived from line WML-EJ11-2553, the method comprising the steps of: (a) preparing a progeny plant derived from line WML-EJ11-2553, wherein said preparing comprises crossing a plant of the line WML-EJ11-2553 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from line WML-EJ11-2553. The plant derived from line WML-EJ11-2553 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from line WML-EJ11-2553 is obtained which possesses some of the desirable traits of the line as well as potentially other selected traits.

In certain embodiments, the present invention provides a method of producing watermelon comprising: (a) obtaining a plant of watermelon line WML-EJ11-2553, wherein the plant has been cultivated to maturity, and (b) collecting watermelons from the plant.

These and other features and advantages of this invention are described in, or are apparent from, the following detailed description of various exemplary embodiments of the devices and methods according to this invention.

DETAILED DESCRIPTION OF THE INVENTION

The invention provides methods and compositions relating to plants, seeds and derivatives of the watermelon line designated WML-EJ11-2553. This line shows uniformity and stability within the limits of environmental influence for the traits described hereinafter. watermelon line WML-EJ11-2553 provides sufficient seed yield. By crossing with a distinct second plant, uniform F1 hybrid progeny can be obtained.

WML-EJ11-2553 is a diploid watermelon inbred with a medium seed size that produces light green fruits with no stripes. It is therefore similar to variety Mickylee, but has smaller size fruits and non-lobed leaves compared to Mickylee having lobed leaves which are more common for watermelon. The line may be beneficially used, for example, as a seed parent for diploid hybrid pollenizers which are used for pollinating commercial fields of Triploid (seedless) watermelon.

WMLEJ11-2553 is widely adapted and performs well under tropical, subtropical and temperate climates. WMLEJ11-2553 may be used as a parent line for diploid hybrid combinations that were to be used as pollen sources for setting seedless fruit on Triploid hybrids in commercial watermelon production fields. A trait desired for such a pollenizer hybrid, and consequently for parent inbreds of such hybrids, is that the fruit of the pollenizer hybrid is easily distinguished from the fruit of all or most Triploid hybrids that the pollenizer could be planted with.

A. Origin And Breeding History of WML-EJ11-2553

The crossing and selections that led directly to WML-EJ11-2553 can be summarized as follows:

WML-EJ11-2553, also known as WMLEJ11-2553, was obtained by pedigree breeding through crossing parental lines Sunshade (U.S. PVP Number 7600027) and WML-110-6741. WML-110-6741 had been developed by Barham Seeds, which was acquired by Seminis Vegetable Seeds Inc.

WML-110-6741 is an inbred with Mickylee type fruits, but that has not been used commercially.

The original cross was done in Woodland, Calif. prior to Year 1. F1 plants were self pollinated in the Woodland Greenhouse in Year 2. F2 plants were self-pollinated in Felda, Fla. in the fall of Year 2. F3 plants were self-pollinated in the Woodland Greenhouse in the spring Year 3. F4 plants were self-pollinated in Woodland, Calif. in the summer of Year 5. F5 plants were self-pollinated in Woodland, Calif. in the summer of Year 6 and F6 seed was harvested as a bulk. The F6 seeds were provided to Foundation Seed department and increased in a cage in the summer of Year 7.

At each generation, selection was made for fruits with no stripes and light green skin color and average to below flesh firmness. Selection was also made for earliness of male flower production and long duration of male flower production.

WML-EJ11-2553 is uniform and stable. A small percentage of variants can occur within commercially acceptable limits for almost any characteristic during the course of repeated multiplication. However no variants are expected.

B. Physiological and Morphological Characteristics of Watermelon Line WML-EJ11-2553

In accordance with one aspect of the present invention, there is provided a plant having the physiological and morphological characteristics of watermelon line WML-EJ11-2553. A description of the physiological and morphological characteristics of watermelon line WML-EJ11-2553 is presented in Table 1.

TABLE 1

Physiological and Morphological Characteristics of Line WML-EJ11-2553

| CHARACTERISTIC | WML-EJ11-2553 | Comparison Variety-Mickey Lee |
|---|---|---|
| 1. Type | round small (icebox) | round small (icebox) |
| 2. Area of best adaptation | | |
| 3. Maturity | | |
| number of days from emergence to anthesis | 49 | 48 |
| number of days from pollination to maturity | 45 | 45 |
| days relative maturity (as reported in seed catalogs) | 97 | 97 |
| category | early | early |
| 4. Ploidy | diploid (Sugar Baby, Yamato 3) | diploid |
| 5. Plant | | |
| cotyledon shape | flat | flat |
| cotyledon: shape | medium elliptic (Crimson Sweet, Farao, Napsugár, Sweet Favorite, Yamato 3) | medium |
| cotyledon: size | large (*Candida*, Farao, Kurobe, Royal flesh hybrid) | medium |
| cotyledon: intensity of green color | medium (Yamato 3) | medium |
| cotyledon: spots | absent (Yamato 3) | absent |
| number of main stems at crown | 3.8 | 4 |
| length of internode | medium (Crimstar, Panonia, Yamato 3) | medium |
| number of staminate flowers per plant at first fruit set | 180.3 | 155.9 |
| number of pistillate flowers per plant at first fruit set | 3.4 | 3.8 |
| number of perfect flowers per plant at first fruit set | 0 | 1 |
| 6. Stem | | |
| shape in cross-section | round | round |
| diameter at second node | 11.4 mm | 10.7 mm |
| surface | pubescent | pubescent |
| cm vine length (at last harvest) | 297.6 cm | 306 cm |
| number of internodes (at last harvest) | 38.2 | 41 |
| ratio: cm vine length ÷ number of internodes (at last harvest) | 7.9 | 7.7 |
| 7. Leaf | | |
| shape | obovate | ovate |
| lobes | none | lobed |
| length | 13 cm | 14.5 cm |
| width | 12.5 cm | 13.3 cm |
| size ratio | longer than wide | longer than wide |
| leaf blade: length (on the $3^{rd}$ leaf when fully developed) | medium (Sugar Baby, Yamato) | long |
| leaf blade: width (on the $3^{rd}$ leaf when fully developed) | medium (*Candida*, Sugar Baby, Yamato 3) | medium |
| leaf blade: ratio length/width (on the $3^{rd}$ leaf when fully developed) | medium (Sugar Baby, Yamato 3) | small |

TABLE 1-continued

Physiological and Morphological Characteristics of Line WML-EJ11-2553

| CHARACTERISTIC | WML-EJ11-2553 | Comparison Variety-Mickey Lee |
|---|---|---|
| dorsal surface pubescence | pubescent | pubescent |
| ventral surface pubescence | pubescent | pubescent |
| color | medium green | dark green |
| RHS color chart value for the leaf color | 147B | 138A |
| leaf blade: color | green (Yamato 3) | gray-green |
| leaf blade: intensity of color | medium (Yamato 3) | dark |
| leaf blade: degree of primary lobing | weak (Rapid) | strong |
| leaf blade: degree of secondary lobing | weak (Daisen) | medium |
| leaf blade: blistering (on 10$^{th}$ to 15$^{th}$ leaf) | strong (Klondike Striped II) | medium |
| leaf blade: marbling | absent or weak (Sugar Baby, Yamato 3) | absent or very weak |
| petiole: length | medium (Kahô, Panonia) | medium |
| 8. Flower | | |
| diameter across the staminate flower | 3.1 cm | 3.1 cm |
| diameter across the pistillate flower | 2.6 cm | 2.7 cm |
| color | yellow | yellow |
| RHS color chart value for flower color | 9C | 5A |
| ovary: size (at the time of flowering) | small | medium |
| ovary: pubescence | strong (Kahô) | strong |
| 9. Mature Fruit | | |
| shape | round | oval |
| fruit: shape in longitudinal section | circular (Kanro, Sugar Baby) | broad elliptic |
| length | 22.7 cm | 23.2 cm |
| diameter at midsection | 19.6 cm | 21.1 cm |
| fruit: weight (1$^{st}$ mature fruit) | low to medium (Pasión) | medium |
| average weight | 4.4 kg | 5.5 kg |
| maximum weight | 5.8 kg | 7.2 kg |
| index = length ÷ diameter × 10 | 11.5 | 10.9 |
| surface | slightly grooved | slightly grooved |
| fruit: distribution of grooves | on whole fruit (Kurobe, Tabata) | at basal half |
| fruit: degree of grooving | strong (Napsugár, Marsowszky, Panni) | weak |
| skin color pattern | solid (one color) | solid (one color) |
| primary skin color | yellow green (Desert King) | light green |
| RHS color chart value for primary skin color | 145B | 147D |
| fruit: ground color* of skin | yellow (Okan, Tayiô) | yellow |
| * Note: the ground color is defined as the lighter color and the color of the stripes as the darker color | | |
| intensity of ground color of skin | light to medium | light |
| stripes | absent (Asahi, Yamato, Marsowszky, Sugar Baby) | absent |
| intensity of marbling | absent or very weak (Napsugár) | absent or very weak |
| 10. Rind | | |
| texture | tough | tough |
| thickness of blossom end | 7.4 mm | 9.2 mm |
| thickness of sides | 7.3 mm | 13.1 mm |
| fruit: thickness of pericarp | medium (Panonia, Sugar Baby, Sugar Belle, Yamato 3) | medium |
| fruit: size of insertion of peduncle | small (Charleston Gray, Sugar Bush) | medium |
| fruit: depression at base | shallow (Kahô, Yellow Baby) | shallow |
| fruit: shape of apical part | flat to rounded | flat to rounded |
| fruit: depression at apex | shallow (Burpee Hybrid, Kahô) | shallow |
| fruit: size of pistil scar | medium (Yamato 3) | small |

TABLE 1-continued

Physiological and Morphological Characteristics of Line WML-EJ11-2553

| CHARACTERISTIC | WML-EJ11-2553 | Comparison Variety-Mickey Lee |
|---|---|---|
| 11. Flesh | | |
| texture | crisp | crisp |
| fruit: firmness of flesh | firm (Fumin) | firm |
| coarseness | fine-little fiber | coarse fibrous |
| fruit: main color of flesh | red (Asahi Yamato, Sugar Baby) | red |
| RHS color chart value for the main flesh color of mature fruit | 39B | N34D |
| fruit: intensity of main color of flesh | medium | light |
| refractometer % soluble solids of juice (center of fruit) | 10.30% | 10.60% |
| % hollow heart | 10% | 0% |
| % placental separation | 30.60% | 47.30% |
| % transverse crack | 0% | 0% |
| fruit: number of seeds | many (Fumin) | medium |
| 12. Seed | | |
| size | medium (Sugar Baby) | small |
| length | 11 mm | 8.7 mm |
| width | 6.7 mm | 5.4 mm |
| thickness | 1.8 mm | 1.8 mm |
| index (index = length ÷ diameter × 10) | 16.4 | 16.1 |
| grams per 1000 seeds | 58.3 g | 49.5 g |
| number of seeds per fruit | 671 | 194.8 |
| color | dark brown | dark brown |
| RHS color chart value for the seed color | 200A | 199C |
| ground color of testa | brown (Otome, Sugar Baby) | brown |
| secondary color of test | present (Charleston Gray) | present |
| distribution of secondary color of testa | in dots only (Charleston Gray, Excel)) | in dots only |
| area of secondary color in relation to that of ground color | medium (Crimson Sweet) | medium |
| patches at hilum | absent (Daisen, Kahô) | absent |
| time of female flowering (50% of plants with at least one female flower) | early | early |
| time of maturity (50% of plants with at least one ripe fruit) | early (Kahô, Sugar Baby) | medium |

*These are typical values. Values may vary due to environment. Other values that are substantially equivalent are within the scope of the invention.

C. Breeding Watermelon Line WML-EJ11-2553

One aspect of the current invention concerns methods for crossing the watermelon line WML-EJ11-2553 with itself or a second plant and the seeds and plants produced by such methods. These methods can be used for propagation of line WML-EJ11-2553, or can be used to produce hybrid watermelon seeds and the plants grown therefrom. Hybrid seeds are produced by crossing line WML-EJ11-2553 with second watermelon parent line.

The development of new varieties using one or more starting varieties is well known in the art. In accordance with the invention, novel varieties may be created by crossing line WML-EJ11-2553 followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) in progeny. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner, true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with line WML-EJ11-2553 and progeny thereof to achieve a homozygous line.

New varieties may be created, for example, by crossing line WML-EJ11-2553 with any second plant and selection of progeny in various generations and/or by doubled haploid technology. In choosing a second plant to cross for the purpose of developing novel lines, it may be desired to choose those plants which either themselves exhibit one or more selected desirable characteristics or which exhibit the desired characteristic(s) in progeny. After one or more lines are crossed, true-breeding lines may be developed.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The line of the present invention is particularly well suited for the development of new lines based on the elite nature of the genetic background of the line. In selecting a second plant to cross with WML-EJ11-2553 for the purpose of developing novel watermelon lines, it will typically be preferred to choose those plants which either themselves exhibit one or more selected desirable characteristics or which exhibit the desired characteristic(s) when in hybrid combination. Examples of desirable characteristics may include, in specific embodiments, high seed yield, high seed germination, seedling vigor, high fruit yield, disease tolerance or resistance, and adaptability for soil and climate conditions. Consumer-driven traits, such as fruit shape, color, texture, and taste are other examples of traits that may be incorporated into new lines of watermelon plants developed by this invention.

D. Further Embodiments of the Invention

In certain aspects of the invention, plants described herein are provided modified to include at least a first desired heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. The term single locus converted plant as used herein refers to those watermelon plants which are developed by a plant breeding technique called backcrossing, wherein essentially all of the desired morphological and physiological characteristics of a variety are recovered in addition to the single locus transferred into the variety via the backcrossing technique.

Backcrossing methods can be used with the present invention to improve or introduce a characteristic into the present variety. The parental watermelon plant which contributes the locus for the desired characteristic is termed the nonrecurrent or donor parent. This terminology refers to the fact that the nonrecurrent parent is used one time in the backcross protocol and therefore does not recur. The parental watermelon plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (non-recurrent parent) that carries the single locus of interest to be transferred. The resulting progeny from this cross are then crossed again to the recurrent parent and the process is repeated until a watermelon plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny watermelon plants of a backcross in which WML-EJ11-2553 is the recurrent parent comprise (i) the desired trait from the non-recurrent parent and (ii) all of the physiological and morphological characteristics of watermelon line WML-EJ11-2553 as determined at the 5% significance level when grown in the same environmental conditions.

Watermelon varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (Plant Physiology, 147: 969-977), for example, and elsewhere, provides a mechanism for integrating single or multiple traits or QTL into an elite line. This molecular breeding-facilitated movement of a trait or traits into an elite line may encompass incorporation of a particular genomic fragment associated with a particular trait of interest into the elite line by the mechanism of identification of the integrated genomic fragment with the use of flanking or associated marker assays. In the embodiment represented here, one, two, three or four genomic loci, for example, may be integrated into an elite line via this methodology. When this elite line containing the additional loci is further crossed with another parental elite line to produce hybrid offspring, it is possible to then incorporate at least eight separate additional loci into the hybrid. These additional loci may confer, for example, such traits as a disease resistance or a fruit quality trait. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and altered nutritional quality. These comprise genes generally inherited through the nucleus.

Direct selection may be applied where the single locus acts as a dominant trait. For this selection process, the progeny of the initial cross are assayed for viral resistance and/or the presence of the corresponding gene prior to the backcrossing. The selection eliminates any plants that do not have the desired gene and resistance trait, and only those plants that have the trait are used in the subsequent backcross. This process is then repeated for all additional backcross generations.

Selection of watermelon plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of watermelon are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., Nucleic Acids Res., 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., Science, 280:1077-1082, 1998).

E. Plants Derived From Watermelon Line WML-EJ11-2553 by Genetic Engineering

Many useful traits that can be introduced by backcrossing, as well as directly into a plant, are those which are introduced by genetic transformation techniques. Genetic transformation may therefore be used to insert a selected transgene into the watermelon line of the invention or may, alternatively, be used for the preparation of transgenes which can be introduced by backcrossing. Methods for the transformation of plants that are well known to those of skill in the art and applicable to many crop species include, but are not limited to, electroporation, microprojectile bombardment, Agrobacterium-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target watermelon cells. The screen disperses the particles so that they are not delivered to the recipient cells in large aggregates. Microprojectile bombardment techniques are widely applicable, and may be used to transform virtually any plant species.

Agrobacterium-mediated transfer is another widely applicable system for introducing gene loci into plant cells. An advantage of the technique is that DNA can be introduced into whole plant tissues, thereby bypassing the need for regeneration of an intact plant from a protoplast. Modern Agrobacterium transformation vectors are capable of replication in E. coli as well as Agrobacterium, allowing for convenient manipulations (Klee et al., Bio-Technology, 3(7):637-642, 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, Agrobacterium containing both armed and disarmed Ti genes can be used for transformation.

In those plant strains where Agrobacterium-mediated transformation is efficient, it is the method of choice because of the facile and defined nature of the gene locus transfer. The use of Agrobacterium-mediated plant integrating vectors to introduce DNA into plant cells is well known in the art (Fraley et al., Bio/Technology, 3:629-635, 1985; U.S. Pat. No. 5,563, 055).

Transformation of plant protoplasts also can be achieved using methods based on calcium phosphate precipitation, polyethylene glycol treatment, electroporation, and combinations of these treatments (see, e.g., Potrykus et al., Mol. Gen. Genet., 199:183-188, 1985; Omirulleh et al., Plant Mol. Biol., 21(3):415-428, 1993; Fromm et al., Nature, 312:791-793, 1986; Uchimiya et al., Mol. Gen. Genet., 204:204, 1986; Marcotte et al., Nature, 335:454, 1988). Transformation of plants and expression of foreign genetic elements is exemplified in Choi et al. (Plant Cell Rep., 13: 344-348, 1994), and Ellul et al. (Theor. Appl. Genet., 107:462-469, 2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for plant gene expression include, but are not limited to, the cauliflower mosaic virus (CaMV) P-35S promoter, which confers constitutive, high-level expression in most plant tissues (see, e.g., Odel et al., Nature, 313:810, 1985), including in monocots (see, e.g., Dekeyser et al., Plant Cell, 2:591, 1990; Terada and Shimamoto, Mol. Gen. Genet., 220:389, 1990); a tandemly duplicated version of the CaMV 35S promoter, the enhanced 35S promoter (P-e35S) the nopaline synthase promoter (An et al., Plant Physiol., 88:547, 1988), the octopine synthase promoter (Fromm et al., Plant Cell, 1:977, 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can also be used for expression of an operably linked gene in plant cells, including promoters regulated by (1) heat (Callis et al., Plant Physiol., 88:965, 1988), (2) light (e.g., pea rbcS-3A promoter, Kuhlemeier et al., Plant Cell, 1:471, 1989; maize rbcS promoter, Schaffner and Sheen, Plant Cell, 3:997, 1991; or chlorophyll a/b-binding protein promoter, Simpson et al., EMBO J., 4:2723, 1985), (3) hormones, such as abscisic acid (Marcotte et al., Plant Cell, 1:969, 1989), (4) wounding (e.g., wunl, Siebertz et al., Plant Cell, 1:961, 1989); or (5) chemicals such as methyl jasmonate, salicylic acid, or Safener. It may also be advantageous to employ organ-specific promoters (e.g., Roshal et al., EMBO J., 6:1155, 1987; Schernthaner et al., EMBO J., 7:1249, 1988; Bustos et al., Plant Cell, 1:839, 1989).

Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a watermelon plant according to the invention. Non-limiting examples of particular genes and corresponding phenotypes one may choose to introduce into a watermelon plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., Biotech. Gen. Engin. Rev., 9:207, 1991). The RNA could also be a catalytic RNA molecule (i.e., a ribozyme) engineered to cleave a desired endogenous mRNA product (see for example, Gibson and Shillito, Mol. Biotech., 7:125, 1997). Thus, any gene which produces a protein or mRNA which expresses a phenotype or morphology change of interest is useful for the practice of the present invention.

F. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Regeneration: The development of a plant from tissue culture.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Self-pollination: The transfer of pollen from the anther to the stigma of the same plant.

Single Locus Converted (Conversion) Plant: Plants which are developed by a plant breeding technique called backcrossing wherein essentially all of the morphological and physiological characteristics of an inbred are recovered in addition to the characteristics conferred by the single locus transferred into the inbred via the backcrossing technique. By "essentially all," it is meant that all of the characteristics of a plant are recovered that are otherwise present when compared in the same environment and save for the converted locus, other than an occasional variant trait that might arise during backcrossing or direct introduction of a transgene. A single locus may comprise one gene, or in the case of transgenic plants, one or more transgenes integrated into the host genome at a single site (locus).

Substantially Equivalent: A characteristic that, when compared, does not show a statistically significant difference (e.g., p=0.05) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a garden watermelon plant by transformation.

G. Deposit Information

A deposit of watermelon line WML-EJ11-2553, disclosed above and recited in the claims, has been made with the American Type Culture Collection (ATCC), 10801 University Blvd., Manassas, Va. 20110-2209, USA, and assigned ATCC Accession No. PTA-120394. The seeds were deposited with the ATCC on Jun. 3, 2013. Access to this deposit will be available during the pendency of the application to the Commissioner of Patents and Trademarks and persons determined by the Commissioner to be entitled thereto upon request. The deposits will be maintained in the ATCC Depository, which is a public depository, for a period of 30 years, or 5 years after the most recent request, or for the enforceable life of the patent, whichever is longer, and will be replaced if it becomes nonviable during that period. Applicant does not waive rights granted under this patent or under the Plant Variety Protection Act (7 U.S.C. 2321 et seq.).

Although the foregoing invention has been described in detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

What is claimed is:

1. A seed of watermelon line WML-EJ11-2553, a sample of seed of said line having been deposited under ATCC Accession Number PTA-120394.

2. A plant of watermelon line WML-EJ11-2553, a sample of seed of said line having been deposited under ATCC Accession Number PTA-120394.

3. A plant part of the plant of claim 2.

4. The plant part of claim 3, wherein said part is selected from the group consisting of a pollen, an ovule, scion, a rootstock, a fruit, and a cell of the plant.

5. A watermelon plant, or a part thereof, having all the physiological and morphological characteristics of the watermelon plant of claim 2.

6. A tissue culture of regenerable cells of watermelon line WML-EJ11-2553, a sample of seed of said line having been deposited under ATCC Accession Number PTA-120394.

7. The tissue culture according to claim 6, comprising cells or protoplasts from a plant part selected from the group consisting of embryos, meristems, cotyledons, pollen, leaves, anthers, roots, root tips, pistil, flower, seed and stalks.

8. A watermelon plant regenerated from the tissue culture of claim 6, wherein the regenerated plant expresses all of the physiological and morphological characteristics of watermelon line WML-EJ11-2553, a sample of seed of said line having been deposited under ATCC Accession Number PTA-120394.

9. A method of producing watermelon seed, comprising crossing the plant of claim 2 with itself or a second watermelon plant.

10. The method of claim 9, wherein the plant of watermelon line WML-EJ11-2553 is the female parent.

11. The method of claim 9, wherein the plant of watermelon line WML-EJ11-2553 is the male parent.

12. An F1 hybrid seed produced by the method of claim 9.

13. An F1 hybrid plant produced by growing the seed of claim 12.

14. A method for producing a seed of a line WML-EJ11-2553-derived watermelon plant comprising the steps of:
   (a) crossing a watermelon plant of line WML-EJ11-2553 with a second watermelon plant, a sample of seed of said line having been deposited under ATCC Accession Number PTA-120394; and
   (b) allowing seed of a WML-EJ11-2553-derived watermelon plant to form.

15. The method of claim 14, further comprising the steps of:
   (c) crossing a plant grown from said WML-EJ11-2553-derived watermelon seed with itself or a second watermelon plant to yield additional WML-EJ11-2553-derived watermelon seed;
   (d) growing said additional WML-EJ11-2553-derived watermelon seed of step (c) to yield additional WML-EJ11-2553-derived watermelon plants; and
   (e) repeating the crossing and growing steps of (c) and (d) to generate further WML-EJ11-2553-derived watermelon plants.

16. A method of vegetatively propagating a plant of watermelon line WML-EJ11-2553 comprising the steps of:
   (a) collecting tissue capable of being propagated from a plant of watermelon line WML-EJ11-2553, a sample of seed of said line having been deposited under ATCC Accession Number PTA-120394;
(b) cultivating said tissue to obtain proliferated shoots; and
(c) rooting said proliferated shoots to obtain rooted plantlets.

17. The method of claim 16, further comprising growing plants from said rooted plantlets.

18. A method of introducing a desired trait into a watermelon plant, said method comprising:
(a) crossing a plant of line WML-EJ11-2553 with a second watermelon plant that comprises a desired trait to produce F1 progeny, a sample of seed of said line WML-EJ11-2553 having been deposited under ATCC Accession Number PTA-120394;
(b) selecting an F1 progeny that comprises the desired trait;
(c) crossing the selected F1 progeny with a plant of line WML-EJ11-2553 to produce backcross progeny;
(d) selecting backcross progeny comprising the desired trait and the physiological and morphological characteristics of watermelon line WML-EJ11-2553; and
(e) repeating steps (c) and (d) three or more times to produce selected fourth or higher backcross progeny that comprise the desired trait.

19. A watermelon plant produced by the method of claim 18.

20. A method of producing a plant of watermelon line WML-EJ11-2553 comprising an added desired trait, the method comprising introducing a transgene conferring the desired trait into a plant of watermelon line WML-EJ11-2553, a sample of seed of said line WML-EJ11-2553 having been deposited under ATCC Accession Number PTA-120394.

21. A seed of the plant of claim 19.

22. A method of producing watermelons comprising:
(a) obtaining the plant of claim 2, wherein the plant has been cultivated to maturity, and
(b) collecting watermelons from the plant.

* * * * *